US006552209B1

(12) United States Patent
Lei et al.

(10) Patent No.: US 6,552,209 B1
(45) Date of Patent: Apr. 22, 2003

(54) PREPARATION OF METAL IMINO/AMINO COMPLEXES FOR METAL OXIDE AND METAL NITRIDE THIN FILMS

(75) Inventors: Xinjian Lei, Vista, CA (US); John Anthony Thomas Norman, Encinitas, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/179,818

(22) Filed: Jun. 24, 2002

(51) Int. Cl.$^7$ ................ C07F 9/00; C07F 7/00
(52) U.S. Cl. ........................... 556/42; 556/51
(58) Field of Search ..................... 556/42, 51

(56) References Cited

U.S. PATENT DOCUMENTS

| | | | |
|---|---|---|---|
| 5,114,750 A | 5/1992 | Howard | 427/226 |
| 5,248,629 A | 9/1993 | Muroyama | 437/52 |
| 5,900,498 A | 5/1999 | Winter et al. | 556/51 |
| 6,015,917 A | * 1/2000 | Bhandari et al. | 556/12 |
| 6,268,288 B1 | 7/2001 | Hautala et al. | 438/680 |

OTHER PUBLICATIONS

Winter, C.H. "The Chemical Vapor Deposition of Metal Films . . . ", Aldrichimica Acta 33: 3–12, 2000.
Sugiyama, K., et al, "Low Temperature Deposition of Metal . . . ", J. Electrochemical Soc. vol. 22, 1545.
Chiu, H.T., et al, "Metal–Organic CVD of Tantalum Oxide . . . ", Chem. Vapor Deposition, vol. 6, 2000.
Park, J.S., et al, "Plasma–Enhanced Atomic Layer Deposition . . . ", J. Electrochem. Soc. vol. 149, 2002.
Bradley, D.C., et al, "Metallo–organic Compounds Containing . . . ", Canadian Journal of Chem., 40: 1962.
Nugent, W.A., et al, "Structure and Reactivity in the Group 5B . . . ", Chem. Commun.: 579, 1978.
Chiu, H.T., et al, "Synthesis and Characterization of Organoimido . . . ", Polyhedron, 17: 1998.
Korolev, A.V., et al, "A General Route to Labile Niobium and . . . ", Inorg. Chem. 36: 1997.

* cited by examiner

*Primary Examiner*—Peter O'Sullivan
(74) *Attorney, Agent, or Firm*—Geoffrey L. Chase

(57) ABSTRACT

This invention relates to an improved process to produce metal imino/amino complexes having the formula $R^1N=M(NR^2R^3)_3$ where M is a pentavalent metal or $(R^1N=)_2M'(NR^2R^3)_2$ where M' is a hexavalent metal. In the process $MX_5$ and two-equivalents of primary amine $R^1NH_2$ or metal hexahalide, $M'X_6$ with seven-equivalents of primary amine $H_2NR^1$ are reacted in the presence of excess pyridine. The resulting reaction product $R^1N=MX_3(py)_2$ or $[(R^1N)_2M'X_2(py)]_2$ then is followed by the addition of $LiNR^2R^3$. The process provides the final product in high yield and in high purity as well as representing a simplified procedure for synthesizing $R^1N=M(NR^2R^3)_3$ or $(R^1N=)_2M'(NR^2R^3)_2$ type complexes.

21 Claims, No Drawings

PREPARATION OF METAL IMINO/AMINO COMPLEXES FOR METAL OXIDE AND METAL NITRIDE THIN FILMS

BACKGROUND OF THE INVENTION

Metal oxide and nitride films have a number of chemical and physical properties, which make their use desirable for a multitude of applications. For instance, the applications of tantalum nitride include its use as wear resistant coatings and as thin layers for diffusion barriers and gate electrodes in integrated circuits. On the other hand, tantalum oxide is considered a candidate material for high dielectric constant thin film applications in microelectronic devices either as a gate dielectric or as the dielectric used in dynamic random access memories (DRAMs) storage capacitors. With the shrinkage of feature sizes in computer chips, chemical vapor deposition (CVD) and atomic layer deposition (ALD) provide a unique advantage over physical vapor deposition in achieving perfectly even and conformal thin films. For the CVD or ALD process to produce tantalum oxide or nitride thin films, both solid and liquid precursors have been utilized so far, but liquid precursors are always preferable due to their ease and repeatability of precursor delivery by either bubbling or direct liquid injection.

The following patents and articles provide the state of the art for the production of metal oxide and metal nitride thin films including compounds of the general formula

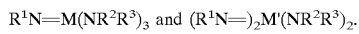

$R^1N=M(NR^2R^3)_3$ and $(R^1N=)_2M'(NR^2R^3)_2$.

U.S. Pat. No. 6,268,288 discloses the production of high quality conformal tantalum nitride films from tantalum halide precursors. In this work, tantalum pentachloride or tantalum pentabromide vapors are contacted with a nitrogen-containing process gas to deposit tantalum nitride films by a thermal CVD process on a substrate heated in the temperature range of 300 to 500° C. Once a thin film of metal nitride is thus grown, a hydrogen plasma anneal is applied to enhance the film quality before the thermal CVD process is repeated. In this way the deposition chemistry is alternated between thermal and plasma cycles until a desired film thickness is achieved. One potential problem with metal halide precursors is that they can leave halide residues in the metal nitride film that can lead to corrosion and other long-term stability problems.

U.S. Pat. No. 5,900,498 discloses the investigation of metal halo-organo complexes in a variation to the above process which teaches the utility of employing metal halo-organo precursors of the formula:

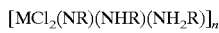

$[MCl_2(NR)(NHR)(NH_2R)]_n$ wherein R is alkyl, cycloalkyl, aryl, alkenyl, cycloalkenyl or $NR^aR^b$ wherein $R^a$ and $R^b$ are independently alkyl, cycloalkenyl or together to form a heterocycle with the nitrogen and M can be tantalum or other suitable metal. Tantalum nitride. films are deposited by the thermal CVD of such single source metal halo-organo precursors, which are prepared by the reaction of tantalum halides with a primary amine or hydrazine. Specifically, the metal halo-organic precursor $[TaCl_2(NBu^t)(NHBu^t)(NH_2Bu^t)]_2$ is prepared by reacting tantalum pentachloride with t-butylamine (~1 mole $TaCl_5/10$ moles $Bu^tNH_2$). The metal halo-organic precursor $[TaCl_2(NNMe_2)(HNNMe_2)(H_2NNMe_2)]_2$ is prepared by reacting tantalum pentachloride with dimethylhydrazine (~1 mole $TaCl_5/6$ moles dimethylhydrazine). Since these metal halo-organic precursors contain halogens there is always the chance of halogen becoming incorporated into the final film.

As disclosed in a review article by Winter et al. (Winter, C. H. "The Chemical Vapor Deposition of Metal Nitride Films Using Modern Metalorganic Precursors." Aldrichimica Acta 33: 3–12, 2000.), tantalum amides have also been chosen as potential precursors for chemical vapor deposition of either tantalum oxide or tantalum nitride. For example, pentakis(diethylamino)tantalum, $Ta(NEt_2)_5$, prepared by reaction of tantalum pentachloride with excess lithium diethylamide, is a liquid at room temperature and has been reported to deposit tantalum nitride thin film by Sugiyama et al. (Sugiyama, K.; Pac, S.; Takahashi, Y.; Motojima, S. "Low Temperature Deposition of Metal Nitrides by Thermal Decomposition of Organometallic Compounds" J. Electrochemical Society, Vol. 122 (1975), 1545.). However, it was found later that the precursor used was actually a mixture consisting of $Ta(NEt_2)_5$, $EtN=Ta(NEt_2)_3$, and $(Et_2N)_3Ta(\eta^2-EtN=CHMe)$, thereby preventing the steady vaporization of just one species to provide a controllable vapor pressure.

U.S. Pat. No. 5,248,629 discloses a process for growing a tantalum oxynitride film by a chemical vapor deposition process using a tantalum amide precursor, pentakis(dimethylamino)tantalum (PDMAT), and ammonia. As with tantalum halides and other metal haloorgano complexes, PDMAT is a solid at room temperature and subsequently suffers from difficulties in providing a constant delivery rate to the reactor chamber. By contrast, tert-(butylimino)tris(diethylamino)tantalum (TBTDET) is a pure liquid at room temperature and has been reported as a precursor to deposit either tantalum oxide or nitride, depending on the CVD process gas used.

Further, Chiu et al. (Chiu, H. T.; Wang, C. N.; Chuang, S. H. "Metal-Organic CVD of Tantalum Oxide from TBTDET and Oxygen" Chem. Vapor Deposition, Vol. 6(2000), 223) disclose the CVD deposition of tantalum oxide thin film using TBTDET and oxygen. Park et al. (Park, J. S.; Park, H. S.; Kang, S. W. "Plasma-Enhanced Atomic Layer Deposition of Ta—N Thin Films" J. Electrochemical Society, Vol. 149(2002), C28–32) describe the plasma enhanced atomic layer deposition (PEALD) of tantalum nitride thin films at a temperature of 260° C. using (TBTDET) and hydrogen radicals. Thus, the tert-butyliminotris(diethylamino) tantalum (TBTDET) type compounds $R^1N=Ta(NR^1R^2)_3$ where $R^1$, $R^2$ and $R^3$ can independently be alkyl or trialkylsilyl are excellent precursors for both the preparation of tantalum oxide and nitride or other tantalum containing thin films by ALD or CVD via reacting vapors of the precursor with a suitable reactive gas at a substrate surface.

Bradley, D. C. and Thomas, I. M. "Metallo-organic Compounds Containing Metal-Nitrogen Bonds, Part III. Dialkylamino Compounds of Tantalum." Canadian Journal of Chemistry. 40: 1355–1360, 1962) disclose metallo-organic compounds containing metal-nitrogen bonds. In this publication, tantalum pentachloride is reacted with five-equivalents of a lithium dialkylamide, $LiNR_2$, e.g., lithium di-n-propylamide or lithium di-n-butylamide to produce the corresponding tantalum pentakisdialkylamide. However, some of those pentakisdialkylamides are unstable at higher temperature and decompose to form $RN=Ta(NR_2)_3$ type complexes with the concomitant release of $RNH_2$.

Nugent, W. A. and Harlow, R. L. "Structure and Reactivity in the Group 5B t-butylimido Complexes $Bu^tN=M(NMe_2)_3$; X-ray Crystal and Molecular structure of t-butylimidotris(dimethylamido)tantalum." Chem. Commun.: 579, 1978 similarly disclose the treatment of $TaCl_5$ with one equivalent of lithium tert-butylamide and four-equivalents of lithium dimethylamide to afford Bu'N=Ta(NMe$_2$)$_3$ in a yield of 40%. However, the poor selectivity and low yield of this procedure prevents its implementation at a large production scale.

Chiu, H. T., Chuang, S. H., Tsai, C. E., Lee, G. H. Peng, S. M. *"Synthesis and Characterization of Organoimido Complexes of Tantalum; Potential Single-source Precursors to Tantalum Nitride."* Polyhedron 17: 2187, 1998 disclose the two-step synthesis of RN=Ta(NEt$_2$)$_3$(R=Bu$^t$, Pr$^i$, or Pr) by reacting TaCl$_5$ with two-equivalents of RNH(Me$_3$Si) in the presence of pyridine (py) overnight to form the intermediate, RN=TaCl$_3$(py)$_2$, followed by reaction with excess of LiNEt$_2$ to replace the three remaining chloride ligands. In this process, RNH(Me$_3$Si) is prepared in situ by the reaction of two equivalents of RNH$_2$ with one equivalent of Me$_3$SiCl. As a result, a total four equivalents of primary amine are used in the process to produce one equivalent of RN=TaCl$_3$(py)$_2$. In addition, high boiling point impurities such as siloxanes which are present in the Me$_3$SiCl end up in the final product from which they are very difficult to remove. Additionally, the by-product RNH$_2$.HCl generated from the preparation of RNH(Me$_3$Si) requires a large amount of solvent(s) to make agitation possible, leading to higher materials costs.

Korolev, A. V., Rheingold, A. L. and William, D. S. "A General Route to Labile Niobium and Tantalum d$^0$ Monoimides. Discussion of Metal-nitrogen Vibrational Modes." *Inorg. Chem.* 36: 2647–2655, 1997 disclose a process for preparing transition metal compounds containing alkyl imido ligands of the formula: RN=MCl$_3$L$_2$ where R is CMe$_2$Et, Bu$^t$ and L is a labile Lewis base. One route shows the reaction of tantalum pentachloride with two equivalents of a primary amine, H$_2$NCMe$_2$Et, and an insoluble inorganic base, e.g., sodium metasilicate, Na$_2$SiO$_3$. Pyridine (py) is added resulting in a product of the formula RN=TaCl$_3$(py)$_2$. However, the insoluble Na$_2$SiO$_3$ solid represents an inefficient heterogeneous absorbent to neutralize the HCl generated in situ since the HCl can only be absorbed on surface sites of the insoluble metasilicate thereby requiring a very large excess of it to effect complete neutralization.

U.S. Pat. No. 5,114,750 discloses a process for making tungsten nitride films utilizing a tungsten imino/amino precursor with a formula of (NHR)$_2$W(NR)$_2$ where R is individually selected from an alkyl group of 1–5 carbon atoms or an aryl group of 5–10 carbon atoms. The precursor can be prepared via reaction of tungsten hexachloride with eleven-equivalents of RNH$_2$. However, the precursor is not thermally stable due to reactive NHR groups.

Therefore, considering all of the above, there exists a need to develop a more efficient and low cost process to synthesize semiconductor grade R$^1$N=M(NR$^2$R$^3$)$_3$ type liquid precursors, especially Bu$^t$N=Ta(NEt$_2$)$_3$. In addition, there also exists a need to efficiently prepare similar (R$^1$N=)$_2$M'(NR$^2$R$^3$)$_2$ type transition metal complexes, such as (Bu$^t$N=)$_2$ M'(NEt$_2$)$_2$. In both R$^1$N=M(NR$^2$R$^3$)$_3$ and (R$^1$N=)$_2$M'(NR$^2$R$^3$)$_2$ type complexes, R$^1$ represents a C$_{1-8}$ alkyl, silylalkyl, cycloalkyl, aryl, alkyl substituted aryl, or NR$^4$R$^5$ wherein R$^4$ and R$^5$ are independently alkyl, cycloalkenyl or R$^4$ and R$^5$ groups are joined in a cyclic form; R$^2$ and R$^3$ represent a C$_{1-8}$ alkyl, silylalkyl, cycloalkyl, aryl, alkyl substituted aryl or R$^2$ and R$^3$ groups are joined in a cyclic form.

BRIEF SUMMARY OF THE INVENTION

This invention relates to an improved process for producing metal imino/amino complexes of the formula R$^1$N=M(NR$^2$R$^3$)$_3$ where M is a pentavalent metal such as those selected from the group consisting of tantalum, niobium, vanadium and other pentavalent transition metals and for producing metal imino/amino complexes of the formula (R$^1$N=)$_2$M'(NR$^2$R$^3$)$_2$ where M' is a hexavalent metal such as tungsten, molybdenum or chromium. The tantalum imino/amino complexes are excellent precursors for producing tantalum nitride, tantalum oxynitride, or tantalum oxide or other tantalum containing thin films in semiconductor applications. The analogous tungsten compounds are potential precursors for tungsten oxide or nitride films grown by ALD or CVD. The improvement comprises:

(a) reacting a metal halide selected from the group consisting of a metal pentahalide MX$_5$ and a metal hexahalide M'X$_6$ with a primary amine H$_2$NR$^1$, or dimethyl hydrazine or tert-butyl hydrazine in the presence of a donating ligand, i.e. a labile Lewis base, such as pyridine to produce intermediate complexes selected from the group consisting of R$^1$N=MCl$_3$(py)$_2$ and [(R$^1$N)$_2$M'Cl$_2$(py)]$_2$, respectively and then, (b) reacting the intermediate complexes with a lithium amide of the formula LiNR$^2$R$^3$ under conditions for forming the respective metal imino/amino complexes selected from the group consisting of R$^1$N=M(NR$^2$R$^3$)$_3$ and (R$^1$N=)$_2$M'(NR$^2$R$^3$)$_2$.

Exemplary steps employing pyridine (py) as a donating ligand are laid out below in equations 1 and 2 for pentavalent metal compounds.

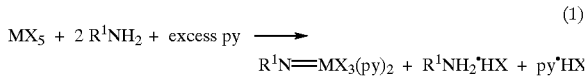
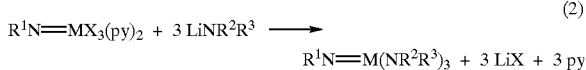

Exemplary steps using py as a donating ligand for hexavalent metal compounds are laid out below in equations 3 and 4.

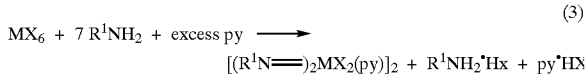
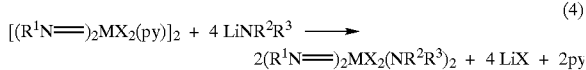

In the above formula X represents a halide such as fluoride, chloride, bromide or iodide, preferably a chloride, whereas R$^1$ represents a C$_{1-8}$ alkyl, silylalkyl, cycloalkyl, aryl, alkyl substituted aryl, or NR$^4$R$^5$ wherein R$^4$ and R$^5$ are independently alkyl, cycloalkenyl or R$^4$ and R$^5$ groups are joined in a cyclic form; R$^2$ and R$^3$ represent a C$_{1-8}$ alkyl, silylalkyl, cycloalkyl, aryl, alkyl substituted aryl or R$^2$ and R$^3$ groups are joined in a cyclic form. The alkyl portion of the groups in the above are selected from the group of C$_{1-8}$ alkyl groups, e.g., methyl, ethyl, propyl, and butyl.

The process, depending upon the specific steps employed, can achieve significant advantages and these include:

an ability to avoid the use of the required large quantities of insoluble inorganic bases such as Na$_2$SiO$_3$ as per literature preparations which contribute to insufficient absorption of HX;

an ability to avoid the use of Me$_3$SiCl as per literature preparations which thereby avoids purification problems resulting from the need to remove high boiling siloxane contaminants from the final liquid product;

in comparison to the literature preparations, it provides an ability to reduce the amount of primary amine employed in the reaction from a typical quantity of four equivalents of amine per one equivalent of ($MX_5$) tantalum pentahalide to only two equivalents of amine per one equivalent of tantalum pentahalide;

in comparison to the literature preparations, it provides an ability to reduce the amount of solvents employed in the reaction;

in comparison to the literature preparations, it provides an ability to reduce the amount of reaction time employed in the reaction; and, in comparison to the literature preparations, it provides an ability to reduce the amount of salts produced in the reaction.

DETAILED DESCRIPTION OF THE INVENTION

The process of the invention involves two steps. The first step is to react metal pentahalide, $MX_5$, with two-equivalents of primary amine ($H_2NR^1$) or the metal hexahalides, $M'X_6$, with seven-equivalents of primary amine, $H_2NR^1$. The reaction is carried out in the presence of a donating ligand (DL) capable of complexing with the respective metal to form the complex represented by the respective formulas, $R^1N=MX_3(DL)_2$ or $[(R^1N)_2M'X_2(DL)]_2$. Dimethyl hydrazine and tert-butyl hydrazine may be used as the functional equivalent of a primary amine.

In a favored reaction the first step is carried out in the presence of a donating ligand (DL), e.g., using an excess of pyridine (py) as the donating ligand in a hydrocarbon solvent to produce a solid comprised of the intermediate complexes $R^1N=MX_3(py)_2$ or $[(R^1N)_2M'X_2(py)]_2$ mixed together with insoluble hydrohalide salts of pyridine py.HX along with hydrohalide salts of primary amine $R^1NH_2.HX$. This mixed solid can be isolated as a solid via centrifugation methods, filtration or stripping off the hydrocarbon solvents. The solid intermediate $R^1N=MX_3(py)_2$ or $[(R^1N)_2M'X_2(py)]_2$ can then be separated by extracting the solid using a suitable solvent and filtering to remove the insoluble by-products $R^1NH_2.HX$ and py.HX.

The second step involves reacting the intermediate complex represented by the formulas $R^1N=MX_3(DL)_2$ or $[(R^1N)_2M'X_2(DL)]_2$ with an excess of lithium amide having the formula of $LiNR^2R^3$ to afford the desired complex, $R^1N=M(NR^2R^3)_3$ or $(R^1N=)_2M'(NR^2R^3)_2$. As will be set forth in greater detail below, the process invention of this disclosure eliminates the need to employ either $Me_3SiCl$ or $Na_2SiO_3$ as halide removing reagents. In addition, the amount of solvent used and reaction time can be reduced significantly with introduction a mixed solvent. The first step is represented in equations 1 and 3 whereas the second step is revealed in equations 2 and 4 for penta- and hexavalent metals respectively:

$$MX_5 + 2 R^1NH_2 + \text{excess py} \longrightarrow \quad (1)$$
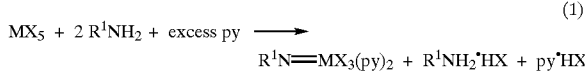

$$R^1N=MX_3(py)_2 + 3 LiNR^2R^3 \longrightarrow \quad (2)$$
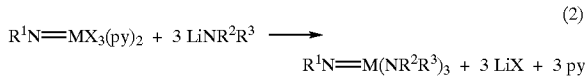

$$MX_6 + 7 R^1NH_2 + \text{excess py} \longrightarrow \quad (3)$$
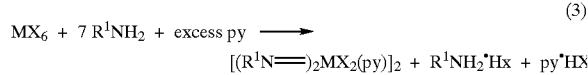

$$[(R^1N=)_2MX_2(py)]_2 + 4 LiNR^2R^3 \longrightarrow \quad (4)$$
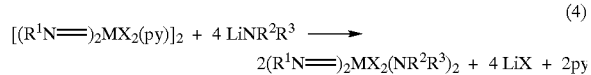

The first step of the process can be run in the temperature range of −40° C. to the boiling point of the hydrocarbon solvent(s) employed typically ~70° C. The exact temperature range of the reaction is dependent on the specific solvent or a combination of organic solvents used and is preferably −40° C. or lower to slow down the initial reaction exotherm. Then, the temperature is gently raised to room temperature.

A variety of primary amines may be used to react with the metal halides as represented in equations 1 and 3 and these include: $C_{1-8}$ alkylamines such as monomethylamine, ethylamine, n-propylamine; i-propylamine, n-butylamine and i and t-butylamine; cycloalkyl amines, such as cyclohexyl amine; and aryl amines such as phenyl amine. For reasons of economy the lower alkyl $C_{1-4}$ amines are preferred. If the primary amines are a gas at room temperature, a solution containing the amines can be employed instead. Furthermore, alkyl derivatives of hydrazine, for example dimethylhydrazine and tert-butylhydrazine can be employed and are contemplated as primary amines.

In forming the intermediate complex, a donating ligand is used to complex with the metal in an effort to facilitate the required coordination number for the metal center and removal of hydrogen halide byproduct as shown in Equations 1 and 3. Although pyridine is a preferred donating ligand for coordination to the metal center plus the removal of HX by-product, other nitrogen containing ligands such as tertiary amines and phosphorus containing ligands such as trialkyl or triaryl phosphines may also be used. Examples of tertiary amines include $C_{1-8}$ alkyl amines, e.g., trimethylamine, triethylamine, and so forth. Trialkyl phosphines include $C_{1-8}$ alkyl phosphines, e.g., trimethylphosphine, triethylphosphine, and so forth. Triarylphosphines include $C_{6-8}$ aryl phosphines, e.g., triphenylphospine $P(C_6H_5)_3$.

Regarding the first step, a mixed solvent in which the reactants are at least partially soluble and the product substantially insoluble is employed to facilitate the reaction. A mixture of toluene and hexane(s) solvents, for example, is employed in an effort to promote the reaction to completion in a short period of time. The reactant $MX_5$ or $M'X_6$ is at least partially soluble in toluene and the reaction product is insoluble in hexane. Separation is accomplished by effecting precipitation of the product, e.g., $R^1N=TaX_3(py)_2$ in the solvent. The ratio of toluene:hexane(s) can vary from 1:1 to 10:1, preferably 1:1 to 4:1, and most preferably about 2:1. The reaction time ranges from 30 minutes to 6 hours, preferably 30 minutes to 2 hours, most preferably is about 1 hour. Other hydrocarbon solvents may be used but these are preferred.

In the second step, the intermediate complex is reacted with a lithium amide of the formula $LiNR^2R^3$. Per the second step, as represented in equations 2 and 4, the lithium amide reactant may be generated as follows: A secondary amine $HNR^2R^3$ is used to react with a solution of an alkyl lithium compounds to generate lithium amide in situ. The selection of the secondary amines is dependent upon the product desired. Exemplary solvents include hexane(s) or other organic solvent. A solution of alkyl lithium can vary from 1 to 10 M in hexane(s), most preferably 2–3 M alkyl lithium, such as but not limited to, n-BuLi or hexyl lithium in hexane(s). Depending upon the choice of solvents employed in the first step, the lithium amide may be formed in situ in the second step, although preformed lithium amide may be used.

The reaction temperature will range from −40° C. to a temperature which is at or below the boiling point of the hydrocarbon solvent(s) employed, typically ~80° C. The optimal temperature of the reaction is dependent on the solvent or a combination of organic solvents, the preferable temperature at the beginning of the reaction is −40° C. The reaction time can be varied from 2 to 24 hours, preferably from 8 to 12 hours.

In the second step, it is preferred that the solvent be selected such that the intermediate reactant and reaction product are at least partially soluble. Preferably the solvent is selected such that the reaction product is sufficiently soluble to form a solution. Typically, the solvent is comprised of a mixture of organics and hydrocarbons with a preferred solvent being comprised of a mixture of tetrahydrofuran (THF) and an organic solvent are used. A ratio of the THF:hexane as the solvent employed in the reaction, for example, can vary, on a volume ratio, from 1:1 to 10:1, preferably 1:1 to 4:1, and most preferably about 2:1. The advantage of using THF is to offer a better reaction medium as well as to reduce the amount of solvent needed. Most importantly, a THF solution of $R^1N=TaX_3(py)_2$, for example, is much easier to transfer from one reaction vessel to another as compared to a slurry of $R^1N=TaX_3(py)_2$ in a single solvent such as hexane. Slurries tend to cause reactor and line plugging adding to processing difficulties.

Although, not intending to be bound by theory, a key advantage in the synthesis of $R^1N=M(NR^2R^3)_3$ or $(R^1N=)_2 M'(NR^2R^3)_2$ type compounds is to form the $R^1N=M$ or $R^1N=)_2M'$ unit by removal of the two halide ligands in $MX_5$ or four halides in $M'X_6$. There are two ways to remove the halide ligands, i.e., in the form of either a halide derivative or a hydrogen halide. As shown in the prior art, $Me_3Si-$ is an excellent halide removal group. On other hand, $Na_2SiO_3$ or other bases are also shown as hydrogen halide acceptors. However, the preparation of $R^1NH(Me_3Si)$, in situ, by the reaction of $R^1NH_2$ with $Me_3SiX$ leads to the formation of a large amount by-product, $R^1NH_2 \cdot HX$, thereby requiring a large amount of solvent to complete the reaction. This also allows for the potential to introduce high molecular weight siloxane impurities, most likely present as contaminants in the $Me_3SiX$ reactant. These siloxanes are very difficult to remove during the following purification process and thereby can contaminate the final liquid product. On the other hand, the insoluble $Na_2SiO_3$ solid represents an inefficient heterogeneous absorbent to neutralize HX generated in situ and is, therefore, required to be used in impractically large amounts.

The following examples are provided to illustrate various and preferred embodiments of the invention and are not intended to restrict the scope thereof.

EXAMPLE 1

Preparation of tert-butyliminotris(diethylamino) tantalum $TaCl_5$ (50 g, 0.14 mol) was loaded in a 500 mL of Schlenk flask. 200 mL of anhydrous toluene was added, resulting in an orange slurry. Tert-butylamine ($Bu^tNH_2$) (28.6 mL, 0.28mol) in 100 mL of hexane was added slowly at low temperature, generating a yellow slurry. The reaction mixture was stirred at reaction temperature (RT) for 10 min. and pyridine (42.7 mL, 0.55 mol) was added. After the mixture was stirred at RT for 1 hr, stripping of solvents was performed to afford a yellow solid. Extraction with 200 mL of THF and filtration via Celite to remove insoluble salts $Bu^tNH_2 \cdot HCl$ or py.HCl gave a yellow solution.

The resulting yellow tetrahydrofuran (THF) solution was slowly added to a hexane solution of lithium diethylamine ($LiNEt_2$) previously freshly prepared in situ by reaction of diethylamine ($HNEt_2$) (46.4 mL, 442 mol) with n-BuLi (2.5M, 176 mL, 442 mol) at low temperature. The reaction mixture turned purple after stirring at room temperature over night. Removal of all solvents gave a dark brown oil with black solid. Extraction with 100 mL of hexane and filtration afford a dark brown solution and a black solid. Stripping off hexane from the dark brown solution gave a dark brown oil. Vacuum distillation at less than 100° C. was applied to give a brown liquid (41 g, yield ~60% based on Ta). Redistillation of the brown liquid afforded a pale yellow liquid.

EXAMPLE 2

Preparation of iso-propyliminotris(diethylamino) tantalum $TaCl_5$ (50 g, 0.14 mol) was loaded in a 500 mL of Schlenk flask. 200 mL of toluene was added which resulted in an orange slurry. Isopropyl amine ($Pr^iNH_2$) (47.7 mL, 0.56 mol) in 100 mL of hexane was added slowly, generating a yellow slurry. The reaction mixture was stirred at RT for 10 min. Pyridine (42.7 mL, 0.55 mol) was added. After the mixture was stirred at RT for 30 min, stripping of solvents was performed to afford a yellow solid. Extraction with 200 mL of THF and filtration via Celite to remove the insoluble salts $Pr^iNH_2 \cdot HCl$ or py.HCl gave a yellow solution.

The resulting yellow THF solution was added to a hexanes solution of $LiNEt_2$ prepared in situ by reaction of $HNEt_2$ (46.4 mL, 442 mol) with n-BuLi (2.5M, 176 mL, 442 mol) at low temperature. The mixture turned brown after stirring at room temperature overnight. Removal of all solvents gave a dark brown oil which was extracted with 100 mL of hexanes. Filtration and stripping off hexanes from the filtrate gave a brown oil. Vacuum distillation at less than 100° C. afforded a yellow liquid (21 g, yield ~33% based on Ta).

EXAMPLE 3

Preparation of Tert-butyliminotris (ethylmethylamino)tantalum

A yellow solution of $Bu^tNTaCl_3(py)_2$ (12.0 g, 23 mmol) in hexanes was added to a hexanes solution of LiNEtMe prepared in situ by reaction of HNEtMe (10.0 mL, 115 mol) with n-BuLi (2.5M, 46 mL, 115 mol) at low temperature. The mixture turned reddish brown after stirring at room temperature over night. Filtration and stripping off hexanes from the filtrate gave a brown oil. Vacuum distillation at 80° C. afforded a yellow liquid (4 g, yield ~45% based on Ta). $^1H$ NMR data ($C_6D_6$, ppm) 3.44(q); 3.16 (s); 1.38(s); 1.11(t).

In summary, as can be noted from Examples 1, 2, and 3, the process described herein provides significant process improvements over many of the prior art procedures.

What is claimed is:

1. In a process for producing a metal imino/amino complex of the formula and selected from the group consisting of $R^1N{=}M(NR^2R^3)_3$ and $(R^1N{=})_2M'(NR^2R^3)_2$ where M and M' are pentavalent or hexavalent metals respectively; $R^1$ is $C_{1-8}$ alkyl, silylalkyl, cycloalkyl, aryl, alkyl substituted aryl, or $NR^4R^5$ wherein $R^4$ and $R^5$ are independently alkyl, cycloalkenyl or $R^4$ and $R^5$ groups are joined in a cyclic form; and, $R^2$ and $R^3$ are individually selected from $C_{1-8}$ alkyl, silylalkyl, cycloalkyl, aryl, alkyl substituted aryl or $R^2$ and $R^3$ groups are joined in a cyclic form, the improvement which comprises:

(a) forming an intermediate complex selected from the group consisting of $R^1N{=}MX_3(DL)_2$ or $((R^1N)_2M'X_2(DL))_2$ by reacting a reaction mixture consisting essentially of a metal halide of the formula and selected from the group consisting of $MX_5$ or $M'X_6$ with an amine consisting essentially of a primary amine of the formula $H_2NR^1$ in the presence of a donating ligand, DL, where M is a pentavalent metal and M' is a hexavalent metal respectively, X is a halide which is selected from the group consisting of fluoride, chloride, bromide and iodide; and $R^1$ is as defined and then, (b) reacting the intermediate complex selected from the group consisting of $R^1N{=}MX_3(DL)_2$ and $((R^1N)_2M'X_2(DL))_2$ with a lithium amide of the formula $LiNR^2R^3$ where $R^2$ and $R^3$ are individually selected from the group consisting $C_{1-8}$ alkyl, silylalkyl, cycloalkyl, aryl, alkyl substituted aryl or $R^2$ and $R^3$ groups are joined in a cyclic form thereby producing said metal imino/amino complex of the formula selected from the group consisting of $R^1N{=}M(NR^2R^3)_3$ and $(R^1N{=})_2M'(NR^2R^3)_2$.

2. The process of claim 1 wherein the metal imino/amino complex is represented by the formula $R^1N{=}M(NR^2R^3)_3$ and M is selected from the group consisting of vanadium, tantalum, and niobium.

3. The process of claim 2 wherein the halide is chloride.

4. The process of claim 3 wherein $R^1$ is $C_{1-8}$ alkyl.

5. The process of claim 4 wherein $R^2$ and $R^3$ are $C_{1-8}$ alkyl.

6. The process of claim 5 wherein $R^1$ is selected from the group consisting of methyl, ethyl, iso-propyl, and t-butyl.

7. The process of claim 6 wherein the donating ligand DL is a nitrogen containing ligand.

8. The process of claim 7 wherein the nitrogen containing ligand is pyridine.

9. The process of claim 8 wherein step (a) is carried out in the presence of a solvent in which the reactants are at least partially soluble and the reaction product is insoluble.

10. The process of claim 9 wherein the reaction in step (a) is carried out in the presence of a solvent comprised of a mixture of toluene:hexane having a volume ratio of from 1–10/1.

11. The process of claim 10 wherein step (b) is carried out in the presence of a solvent comprised of a mixture of tetrahydrofuran:hexane having a volume ratio of from 1–10/1.

12. The process of claim 6 wherein the metal M is tantalum.

13. The process of claim 12 wherein $R^1$ is ethyl, isopropyl or t-butyl.

14. The process of claim 13 wherein $R^2$ and $R^3$ are methyl or ethyl.

15. The process of claim 1 wherein the metal imino/amino complex is represented by the formula $(R^1N{=})_2M'(NR^2R^3)_2$.

16. The process of claim 15 wherein the hexavalent metal M' is selected from the group consisting of chromium, molybdenum, and tungsten.

17. The process of claim 15 wherein the halide is chloride.

18. The process of claim 15 wherein $R^1$ is methyl, iso-propyl, or t-butyl and $R^2$ and $R^3$ are methyl or ethyl.

19. The process of claim 18 wherein the metal M' is tungsten.

20. The process of claim 19 wherein the donating ligand is a nitrogen containing ligand.

21. The process of claim 20 wherein the nitrogen containing compound is pyridine.

* * * * *